(12) United States Patent
Burton et al.

(10) Patent No.: US 10,427,147 B2
(45) Date of Patent: Oct. 1, 2019

(54) SMALL CRYSTAL, HIGH SURFACE AREA EMM-30 ZEOLITES, THEIR SYNTHESIS AND USE

(71) Applicant: ExxonMobil Research and Engineering Company, Annandale, NJ (US)

(72) Inventors: Allen W. Burton, Stewartsville, NJ (US); Karl G. Strohmaier, Port Murray, NJ (US); Mobae Afeworki, Phillipsburg, NJ (US); Christine E. Kliewer, Clinton, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 186 days.

(21) Appl. No.: 15/408,802

(22) Filed: Jan. 18, 2017

(65) Prior Publication Data

US 2017/0240431 A1    Aug. 24, 2017

Related U.S. Application Data

(60) Provisional application No. 62/297,181, filed on Feb. 19, 2016.

(51) Int. Cl.
| | | |
|---|---|---|
| C01B 39/36 | (2006.01) | |
| B01J 20/18 | (2006.01) | |
| B01J 29/40 | (2006.01) | |
| C01B 39/40 | (2006.01) | |
| B01J 37/10 | (2006.01) | |
| C01B 39/48 | (2006.01) | |
| C01B 37/02 | (2006.01) | |
| C07C 211/63 | (2006.01) | |
| B01J 20/30 | (2006.01) | |
| B01J 29/70 | (2006.01) | |
| B01J 37/00 | (2006.01) | |
| B01J 37/04 | (2006.01) | |

(52) U.S. Cl.
CPC .............. *B01J 37/10* (2013.01); *B01J 20/18* (2013.01); *B01J 20/3085* (2013.01); *B01J 29/40* (2013.01); *B01J 29/70* (2013.01); *B01J 37/009* (2013.01); *B01J 37/0018* (2013.01); *B01J 37/04* (2013.01); *C01B 37/02* (2013.01); *C01B 39/36* (2013.01); *C01B 39/365* (2013.01); *C01B 39/40* (2013.01); *C01B 39/48* (2013.01); *C07C 211/63* (2013.01); *C01P 2004/64* (2013.01); *C01P 2006/12* (2013.01)

(58) Field of Classification Search
CPC ....... C01B 39/36; C01B 39/365; C01B 39/40; B01J 29/40; B01J 20/18
See application file for complete search history.

(56) References Cited

U.S. PATENT DOCUMENTS

| | | | |
|---|---|---|---|
| 3,702,886 A | 11/1972 | Argauer et al. | |
| 3,709,979 A | 1/1973 | Chu | |
| RE29,948 E | 3/1979 | Dwyer et al. | |
| 4,537,754 A | 8/1985 | Casci et al. | |
| 7,767,192 B1* | 8/2010 | Verduijn | C01B 37/02 423/702 |
| 2010/0119736 A1* | 5/2010 | Yan | C01B 39/36 427/595 |
| 2013/0059722 A1* | 3/2013 | Tsapatsis | B01J 29/40 502/4 |
| 2015/0298981 A1* | 10/2015 | Burton | C01B 37/02 585/250 |
| 2016/0199824 A1* | 7/2016 | Yoshida | B01J 29/40 585/476 |
| 2017/0341948 A1* | 11/2017 | Lewis | B01J 29/84 |

FOREIGN PATENT DOCUMENTS

WO    2015029355 A1    5/2010

OTHER PUBLICATIONS

Partial International Search Report and Written Opinion PCT/US2017/013879 dated Apr. 6, 2017.
Deluca et al., "Direct formation of self-bonded pellets during the synthesis of mordenite and ZSM-11 zeolites from low water content systems", Microporous and Mesoporous Materials, Jan. 1, 2001, pp. 37-48, vol. 42, No. 1, Elsevier.
Serrano et al., "Synthesis of hierarchical ZSM-5 by silanization and alkoxylation of protozeolitic units", Catalysis Today, Dec. 13, 2010, pp. 86-95, vol. 168, No. 1, Elsevier.
International Search Report and Written Opinion PCT/US2017/013879 dated Jul. 7, 2017.
Nakayama, "Hydates of Organic Compounds. IV. Clathrate Hydrates of Various Bolaform Salts", Bulletin of the Chemical Society of Japan, Jan. 1, 1979, pp. 52-56, vol. 52, No. 1, Chemical Society of Japan.
Iwaguchi, "Supporting Electrolyte of Polarography. Depolarized Potentials of Hexamethylenebis(trialkylammonium Halide)." Journal of the Pharmaceutical Society of Japan Apr. 2011, Jan. 1, 1961, pp. 925-927, vol. 81, No. 6, The Pharmaceutical Society of Japan.
Bonilla et al., "Zeolite (MFI) Crystal Morphology Control Using Organic Structure-Directing Agents", Chemistry of Materials, Dec. 28, 2004, vol. 16, No. 26, ACS Publications.
Kim et al., "Effect of mesoporosity against the deactivation of MFI zeolite catalyst during the methanol-to-hydrocarbon conversion process", Journal of Catalysis, 2010, pp. 219-228, vol. 269, Elsevier, ScienceDirect.

(Continued)

Primary Examiner — David M Brunsman
(74) Attorney, Agent, or Firm — Amanda K. Norwood

(57) ABSTRACT

A process is disclosed for producing small crystal, high surface area crystalline materials having the MFI and/or MEL framework-type, designated as EMM-30, using as a structure directing agent tetrabutylammonium cations and/or tetrabutylphosphonium cations, or 1,5-bis(N-tributylammonium)pentane dications, and/or 1,6-bis(N-tributylammonium)hexane dications. The compositions made according to that process, as well as the various dication compositions themselves, are also disclosed.

12 Claims, 11 Drawing Sheets

(56) References Cited

OTHER PUBLICATIONS

Firoozi et al."The effect of micro and nano particle sizes of H-ZSM-5 on the selectivity of MTP reaction", Catalysis Communications, 2009, pp. 1582-1585, vol. 10, Elsevier, ScienceDirect.
Serrano et al., "Molecular and Meso- and Macroscopic Properties of Hierarchical Nanocrystalline ZSM-5 Zeolite Prepared by Seed Silanization", Chemistry of Materials, Jan. 28, 2009, pp. 641-654, vol. 21, ACS Publications.
Choi et al., "Stable single-unit-cell nanosheets of zeolite MFI as active and long-lived, catalysts", Nature, Sep. 10, 2009, pp. 246-249, vol. 461, Springer Nature.
Zhang et al., "Synthesis of Self-Pillared Zeolite Nanosheets by Repetitive Branching", Science, Jun. 29, 2012, pp. 1684-1687, vol. 336, American Association for the Advancement of Science.
Lippens et al., "Studies on pore systems in catalysts: V. The t method", Journal of Catalysis, Jun. 1965, pp. 319-323, vol. 4, 319, Elsevier, ScienceDirect.
Parikh et al., Non-thermal calcination by ultraviolet irradiation in the synthesis of microporous materials, Microporous and Mesoporous Materials, 2004, pp. 17-22, vol. 76, Elsevier, Science Direct.

\* cited by examiner

SMALL CRYSTAL, HIGH SURFACE AREA EMM-30 ZEOLITES, THEIR SYNTHESIS AND USE

CROSS-REFERENCE TO RELATED APPLICATIONS

This application claims priority to U.S. Provisional Application Ser. No. 5 62/297,181 filed on Feb. 19, 2016, herein incorporated by reference in its entirety.

FIELD

This invention relates to small crystal size, high surface area MFI and/or MEL framework-type crystalline materials, designated as EMM-30, their synthesis and their use as adsorbents and catalysts for organic conversion reactions.

BACKGROUND

Crystalline materials are classified by the Structure Commission of the International Zeolite Association according to the rules of the IUPAC Commission on Zeolite Nomenclature. According to this classification, framework type zeolites and other crystalline microporous crystalline materials, for which a structure has been established, are assigned a three letter code and are described in the Atlas of Zeolite Framework Types, Sixth Revised Edition, Elsevier (2007).

One known crystalline material for which a structure has been established is the material designated with MFI framework-type, most notably including ZSM-5. Crystalline ZSM-5 and its conventional preparation using tetrapropylammonium cations as a structure directing agent, are taught by U.S. Pat. No. 3,702,886 and RE 29,948, the entire disclosures of which are incorporated herein by reference. Conventional ZSM-5 has a distinctive X-ray diffraction pattern which distinguishes it from other known crystalline materials and is a highly versatile catalyst useful in a variety of organic conversion reactions.

Another known crystalline material structure is MEL, also known as ZSM-11, which is described in detail in U.S. Pat. No. 3,709,979, the entire disclosure of which is incorporated herein by reference. MFI and MEL framework-type crystalline materials have similar structures and are frequently co-produced in zeolite synthesis processes as intergrown or disordered materials.

For some acid-catalyzed reactions over zeolites, it is beneficial to reduce diffusion lengths of the reagent and/or product molecules by employing a zeolite with a reduced crystal size and hence an increased external surface area. This may have the effect of reducing the shape selective effects of the zeolite, but for reactions that require only strong activity this may not be important. For example, the increased external surface area permits reactions with larger molecules that cannot enter the pores of the zeolite. In addition, in some processes it has been observed that the rate of deactivation is reduced when the external surface area of the ZSM-5 zeolite is increased. See, for example, M. Choi et al, Nature 461 (2009) 246-249 J. Kim, M. Choi, R. Ryoo, J. Catal. 269 (2010) 219-228). Increased external surface area has also been reported to improve the propylene yields in methanol conversion. See, for example, M. Firoozi et al. Catal. Commun. 10 (2009) 1582-1585.

An example of small crystal ZSM-5 is disclosed in U.S. Pat. No. 5,240,892, in which the ZSM-5 is in the form of platelets having first and second major dimensions of at least about 0.05 micron, preferably at least about 0.1 micron, and a minor third dimension of less than about 0.02 micron, preferably less than about 0.01 micron. The ZSM-5 has a mesitylene sorption capacity of at least 3.0 weight % and is produced using precipitated silica as the silica source either in the absence of an organic directing agent or using n-propylamine as the directing agent.

In addition, in Chem. Mater. 21 (2009) 641-654, D. Serrano et al. claim synthesizing ZSM-5 crystals as small as 5 to 10 nm using a dual template of tetrapropylammonium (TPA) ions and phenylaminopropyltrimethoxysilane. In this method, the silanizing agent is introduced after the synthesis gel is pre-heated for short periods of time before the onset of zeolite crystallization. FIG. 1 of Serrano et al. shows a schematic representation of the crystallized products, whereas FIG. 2 shows TEM images of the product. Although these TEM images show very small particles, the peaks in the powder XRD of the product from this work are consistent with crystals exceeding 5 to 10 nm in their dimensions.

Ryoo and coworkers have reported in "Stable single-unit-cell nanosheets of zeolite MFI as active and long-lived, catalysts", Nature, 461, 246-249 (10 Sep. 2009), the synthesis of a single unit cell-thick version of ZSM-5 by using a single templating agent composed of a 22-carbon atom alkyl chain and two quaternary ammonium groups separated by a methylene chain of 6 carbon atoms. Here the quaternary ammonium groups are located within the single-unit cell nanosheets, which are separated from one another by the long alkyl chains. FIG. 3 of Ryoo et al. shows a schematic of the unilamellar and multilamellar version of the ZSM-5 crystals that are a single unit cell in thickness.

U.S. Patent Application Publication No. 2015/0298981 describes a crystalline material designated as EMM-20 and having the framework structure of ZSM-5 comprising crystals having an external surface area in excess of 100 $m^2/g$ (as determined by the t-plot method for nitrogen physisorption) and a unique X-ray diffraction pattern. The crystalline material may be synthesized in the presence of an organic structure directing agent (Q) selected from one or more of 1,4-bis(N-pentylpyrrolidinium)butane dications, 1,5-bis(N-pentylpyrrolidinium)pentane dications, or 1,6-bis(N-pentylpyrrolidinium)hexane dications.

In 2012, Zhang et al. reported the synthesis of a "self-pillared" MFI or WI/MEL-type materials using tetrabutylphosphonium hydroxide (TBPOH) and/or tetrabutylammonium (TBAOH) as the structure-directing agent (SDA). See "Synthesis of Self-Pillared Zeolite Nanosheets by Repetitive Branching", Science, 336 (2012), 1684-1687. TEM of the reported products shows a morphology composed of thin sheets of zeolite that are about 1 unit cell in width. The thin sheets interpenetrate one another at right angles to form a cross-hatched network of crystals with mesopores between them that are 2-7 nm in size. The resulting "house-of-cards" arrangement of the nanosheets creates a permanent network of 2- to 7-nanometer mesopores, which, along with the high external surface area and reduced micropore diffusion length, account for higher reaction rates for bulky molecules relative to those of other mesoporous and conventional MFI zeolites. The publication reported only materials with gel Si/Al 75.

Despite these advances, a need still exists for new ultra-small crystal forms of MFI and MEL framework-type crystalline materials with higher external surface areas and to extend the Si/Al range over which these materials can be synthesized.

SUMMARY

According to the invention, it has now been found that, although the self-pillaring effect observed by Zhang et al. is difficult to reproduce particularly at gel Si/Al ratios <75, high surface area MFI and/or MEL framework-type crystalline materials can still be produced at low Si/Al ratios using TBPOH and TBAOH as the SDA by reducing the water content and/or the Group 1 cation level of the gel. In addition, it has been found that high surface area MFI and/or MEL framework-type crystalline materials can also be produced using the novel SDAs, 5-bis(N-tributylammonium) pentane dications and/or 1,6-bis(N-tributylammonium) hexane dications. In fact, in some cases it has been possible to produce MFI and/or MEL framework-type crystalline materials with external and/or total surface areas higher than previously reported.

Thus, in a first aspect, the invention resides in a process for producing a crystalline material having the MFI and/or MEL framework-type, the process comprising: (i) preparing a synthesis mixture capable of forming the crystalline material, the mixture comprising a source of an oxide of a tetravalent element Y, optionally a source of a trivalent element X, optionally a source of the trivalent element X, optionally a source of an alkali or alkaline earth metal (M), water, and a directing agent ($Q_1$) comprising tetrabutylammonium cations, and/or tetrabutylphosphonium cations, wherein the synthesis mixture has at least one of (a) $H_2O/YO_2$ molar ratio of less than 10, and (b) $YO_2/X_2O_3$ molar ratio of less than 150; (ii) heating the mixture under crystallization conditions including a temperature of from 80° C. to 220° C. and a time from 1 day to 28 days until crystals of the crystalline material are formed; and (iii) recovering the crystalline material from step (ii).

In a second aspect, the invention resides in a process for producing a crystalline material having the MFI and/or MEL framework-type, the process comprising: (i) preparing a synthesis mixture capable of forming the crystalline material, said mixture comprising a source of an oxide of a tetravalent element Y, optionally a source of a trivalent element X, optionally a source of an alkali or alkaline earth metal (M), water, and a directing agent ($Q_2$) comprising 1,5-bis(N-tributylammonium)pentane dications, and/or 1,6-bis(N-tributylammonium)hexane dications; (ii) heating the mixture under crystallization conditions including a temperature of from 80° C. to 220° C. and a time from 1 day to 28 days until crystals of the crystalline material are formed; and (iii) recovering the crystalline material from step (ii).

In a third aspect, the invention resides in a crystalline material having within its pore structure 1,5-bis(N-tributylammonium)pentane dications, and/or 1,6-bis(N-tributylammonium)hexane dications.

In a fourth aspect, the invention resides in a crystalline material having the MFI and/or MEL framework-type and a chemical composition comprising the molar relationship (n)$YO_2$:$X_2O_3$, wherein n is a number of at least 20 and less then 2000, for example less than 150, X is a trivalent element and Y is a tetravalent element and wherein the crystalline material comprises crystals having a total surface area (as determined by the t-plot method for nitrogen physisorption) in excess of 770 $m^2/g$ and/or an external surface area (as determined by the t-plot method for nitrogen physisorption) in excess of 400 $m^2/g$.

In a fifth aspect, the invention resides in an organic nitrogen compound comprising a dication having formula (I) or (II):

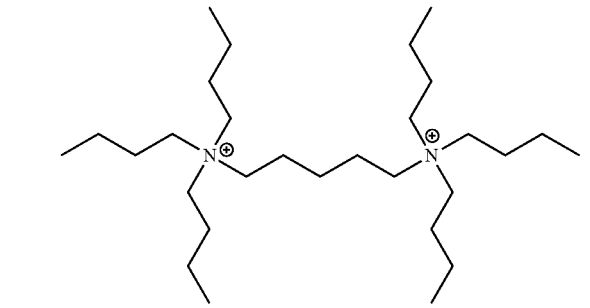

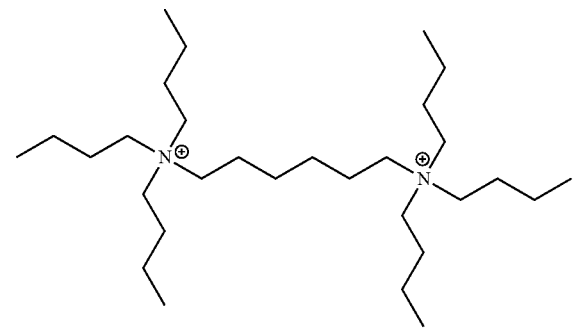

DETAILED DESCRIPTION OF THE EMBODIMENTS

Figure 1A:
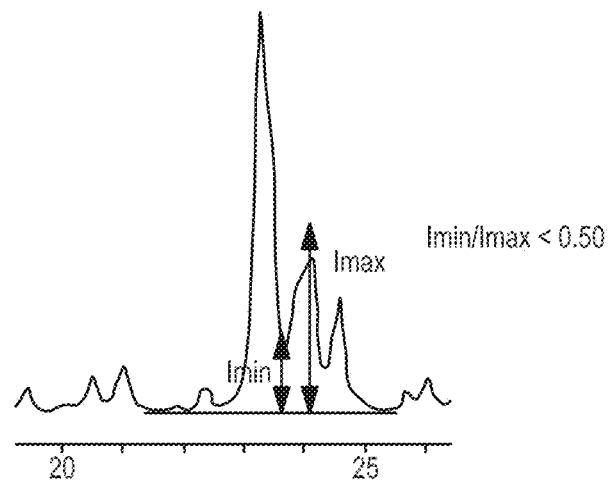
FIGS. 1 (a) and (b) show the portions of the X-ray pattern of a conventional ZSM-5 product made according to U.S. Pat. No. 5,240,892 in the regions 20 to 28 degree two theta and 5 to 10 degrees two theta respectively.

Described herein are processes of producing crystalline materials having an MFI and/or MEL framework-type and to small crystal forms of such crystalline materials having uniquely high external and/or total surface areas.

In some embodiments, the crystalline phase of the crystalline material produced by the present process comprises substantially MFI framework-type material, particularly ZSM-5. In some embodiments, the crystalline phase of the crystalline material may contain non-trivial quantities of MEL framework-type material, particularly ZSM-11, such as at least 5 wt %, or at least 10 wt %, or at least 20 wt %, or at least 30 wt %, or at least 40 wt %, or at least 50 wt %, or at least 60 wt %, or at least 70 wt %, or at least 80 wt %, or at least 90 wt % of MEL framework-type material. In some embodiments, the crystalline phase of the crystalline material produced by the present process can comprise substantially entirely MEL framework-type material, particularly ZSM-11.

As conventionally synthesized, for example in the presence of tetrapropylammonium cations as taught by U.S. Pat. No. 3,702,886 and RE 29,948, a typical preparation of ZSM-5 has an X-ray diffraction pattern including the characteristic lines listed in Table 1 below:

TABLE 1

| Interplanar d-Spacing (Å) | Two-theta (degrees) | Relative Intensity (100 × I/Io) |
|---|---|---|
| 11.10 ± 0.25 | 7.98 ± 0.17 | s-vs |
| 9.85 ± 0.30 | 9.03 ± 0.28 | m-vs |
| 6.70 ± 0.10 | 13.22 ± 0.20 | w |
| 6.34 ± 0.10 | 14.06 ± 0.22 | w |
| 5.98 ± 0.10 | 14.81 ± 0.25 | w |
| 5.57 ± 0.10 | 15.91 ± 0.29 | w |
| 5.00 ± 0.10 | 17.74 ± 0.36 | w |
| 4.36 ± 0.10 | 20.38 ± 0.48 | w |
| 4.25 ± 0.08 | 20.90 ± 0.40 | w |
| 4.08 ± 0.05 | 21.79 ± 0.27 | w |
| 3.85 ± 0.07 | 23.08 ± 0.46 | m-vs |
| 3.71 ± 0.05 | 23.99 ± 0.33 | w-m |
| 3.62 ± 0.04 | 24.59 ± 0.27 | w |
| 3.04 ± 0.03 | 29.39 ± 0.30 | w |
| 2.99 ± 0.02 | 29.89 ± 0.21 | w |

As conventionally synthesized, for example in the presence of tetrabutylammonium cations as taught by U.S. Pat. No. 3,709,979, a typical preparation of ZSM-11 has an X-ray diffraction pattern including the characteristic lines listed in Table 2 below:

TABLE 2

| Interplanar d-Spacing (Å) | Relative Intensity (100 × I/Io) |
|---|---|
| 11.2 ± 0.2 | m |
| 10.1 ± 0.2 | m |
| 6.73 ± 0.2 | w |
| 5.75 ± 0.1 | w |
| 5.61 ± 0.1 | w |
| 5.03 ± 0.1 | w |
| 4.62 ± 0.1 | w |
| 4.39 ± 0.08 | w |
| 3.86 ± 0.07 | vs |
| 3.73 ± 0.07 | m |

TABLE 2-continued

| Interplanar d-Spacing (Å) | Relative Intensity (100 × I/Io) |
|---|---|
| 3.49 ± 0.07 | w |
| 3.07 ± 0.05 | w |
| 3.00 ± 0.05 | w |
| 2.01 ± 0.02 | w |

The crystalline material produced by the inventive process may have X-ray diffraction peaks solely associated with ZSM-5 (WI) and/or with ZSM-11 (MEL) materials. In particular, the crystalline material produced by the inventive process may, in its as-synthesized form, exhibit an X-ray diffraction pattern including the characteristic peak maxima listed in Table 3 below:

TABLE 3

| Interplanar d-Spacing (Å) | Two-theta (degrees) | Relative Intensity (100 × I/Io) |
|---|---|---|
| 11.10 ± 0.25 | 7.98 ± 0.17 | s-vs |
| 9.85 ± 0.30 | 9.03 ± 0.28 | m-vs |
| 6.70 ± 0.10 | 13.22 ± 0.20 | w |
| 6.34 ± 0.10 | 14.06 ± 0.22 | w |
| 5.98 ± 0.10 | 14.81 ± 0.25 | w |
| 5.57 ± 0.10 | 15.91 ± 0.29 | w |
| 5.00 ± 0.10 | 17.74 ± 0.36 | w |
| 4.36 ± 0.10 | 20.38 ± 0.48 | w |
| 4.25 ± 0.08 | 20.90 ± 0.40 | w |
| 4.08 ± 0.05 | 21.79 ± 0.27 | w |
| 3.85 ± 0.07 | 23.08 ± 0.46 | m-vs |
| 3.71 ± 0.05 | 23.99 ± 0.33 | w-m |
| 3.62 ± 0.04 | 24.59 ± 0.27 | w |
| 3.04 ± 0.03 | 29.39 ± 0.30 | w |
| 2.99 ± 0.02 | 29.89 ± 0.21 | w |

The X-ray diffraction data reported herein were collected with a Panalytical X'Pert Pro™ diffraction system with an Xcelerator™ multichannel detector, equipped with a germanium solid state detector, using copper K-alpha radiation. The diffraction data were recorded by step-scanning at ~0.02 degrees two-theta, where theta is the Bragg angle, and using an effective counting time of ~2 seconds for each step. The interplanar spacings, d-spacings, were calculated in Angstrom units, and the relative intensities of the lines, $I/I_0$, represents the ratio of the peak intensity to the intensity of the strongest line, above background. The intensities are uncorrected for Lorentz and polarization effects. The relative intensities are given in terms of the symbols vs=very strong (75-100), s=strong (50-74), m=medium (25-49) and w=weak (0-24). In certain embodiments, one, some, or all of the relative intensities indicated as including w (weak) can be non-zero values.

It is known that certain lines in the X-ray patterns of zeolites can tend to broaden as the relevant dimension of the zeolite crystal decreases, so that adjacent lines may begin to overlap and thereby appear as only partially resolved peaks or as unresolved broad peaks. In certain embodiments of the crystalline materials described herein, particularly the ultra-small crystal materials described below, this line broadening may result in there being only a single diffuse composite feature in the two-theta range from about 21.5° to about 26° (d-spacing range from ~4.13 Å to ~3.42 Å) of the X-ray pattern. In such cases, the maximum of the composite peak near 24.0±0.30 degrees two-theta and the maximum of the composite peak near 24.6±0.30 degrees two-theta can either appear as shoulders or can form part of a large diffuse composite peak with a maximum near 23.1 (±0.20) degrees two-theta.

In a powder XRD pattern of a typical (larger crystallite) ZSM-5 sample, the composite peak with a maximum near 23.1 degrees two-theta and the composite peak near 24.0 degrees two-theta can intersect to form a clearly visible local minimum [see FIG. 1(a)]. In these typical ZSM-5 preparations, the ratio of the relative background-subtracted intensity of this local minimum ($I_{min}$) to the relative background-subtracted intensity of the composite peak near 24.0 degrees two-theta ($I_{max}$) can be less than 0.40 in both the as-made and calcined forms of the zeolite product. In some embodiments of the present ultra-small crystal material, the local minimum may still be clearly discerned from the composite peak near 24.0 degrees two-theta, even where the $I_{min}/I_{max}$ ratio can be at least about 0.70. In certain embodiments, the crystals can become so small and the peaks so severely broadened that the peak maximum near 24.0 degrees two-theta either can appear as an inflection point of the large diffuse composite peak with a maximum near 23.1 (±0.20) degrees two-theta or can evidence no local maximum or inflection point for the composite peak near 24.0 (±0.30) degrees two-theta. In these extreme cases, the $I_{min}/I_{max}$ ratio can approach 1.0.

Figure 1B:
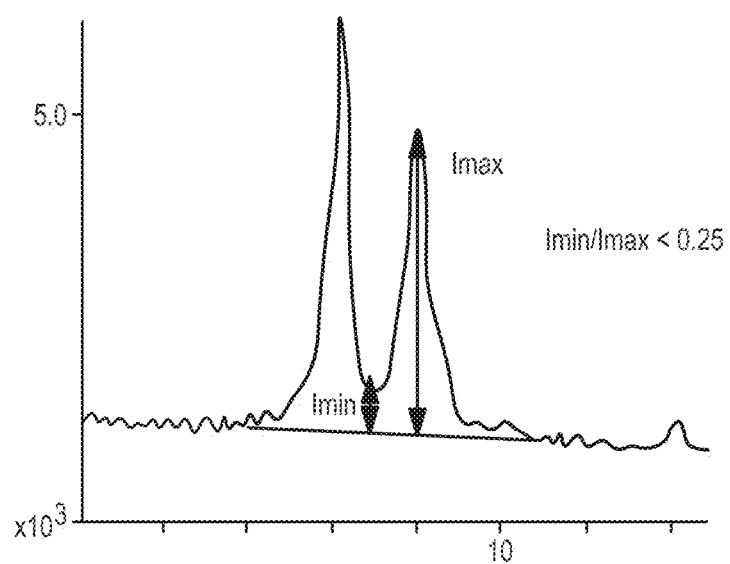

Similarly, in typical ZSM-5 preparations, the composite peak with a maximum near 7.96 (±0.30) degrees two-theta and the composite peak with a maximum near 8.90 (±0.30) degrees two-theta can intersect to form a clearly visible local minimum [see FIG. 1(b)], in which the ratio of the relative background-subtracted intensity of this local minimum ($I_{min}$) to the relative background-subtracted intensity of the composite peak near 8.90 degrees two-theta ($I_{max}$) can be less than 0.20 in both the as-made and calcined forms of the zeolite. In contrast, in the calcined version of the inventive ultra-small crystal material, the $I_{min}/I_{max}$ ratio can be at least 0.20, or greater than 0.20. In certain situations (with the inventive ultra-small crystals), the $I_{min}/I_{max}$ ratio can be at least 0.40. It should be borne in mind that, in cases where preferred orientation effects may be present, care should be taken to reduce/minimize their effects on X-ray patterns.

Most of the syntheses described herein produce MFI and/or MEL framework-type crystalline materials having a small crystal, such that the total surface area of the crystalline phase can be at least about 500 m²/g and external surface area can be at least about 150 m²/g. However, in certain ultra-small crystal embodiments of the present invention, the crystalline materials described herein can comprise crystals having a total surface area of least about 750 m²/g, for example at least about 770 m²/g or at least about 800 m²/g, such as from about 800 m²/g to about 1500 m²/g. Alternatively or additionally, the ultra-small crystalline materials described herein may comprise crystals having an external surface area of at least 350 m²/g, for example at least about 400 m²/g or at least about 450 m²/g, such as from about 450 m²/g to about 1200 m²/g or from about 500 m²/g to about 1000 m²/g. Such values are believed to be higher than any previously reported for MFI and MEL framework-type crystalline materials. All surface area values given herein are determined from nitrogen physisorption data using the t-plot method. Details of this method can be found in Lippens, B. C. and deBoer, J. H., "Studies on pore systems in catalysts: V. The t method", *J. Catal.*, 4, 319 (1965), the entire contents of which are incorporated herein by reference.

Because the syntheses described herein produce such ultra-small crystal sizes (e.g., less than 50 microns), any crystal size measurements/distributions should be (and are herein) done using a transmission electron microscope (TEM) in transmission mode. Average crystal size (diameter) measurements represent a mean of size (diameter) measurements made on at least 100 different crystals. Thus, in certain ultra-small crystal embodiments of the present invention, the crystalline materials described herein can comprise crystals having average sizes (diameters) of about 35 nm or less (e.g., about 30 nm or less, about 25 nm or less, about 20 nm or less, about 15 nm or less, or about 10 nm or less) and optionally at least about 3 nm (e.g., at least about 4 nm, at least about 5 nm, at least about 6 nm, at least about 7 nm, at least about 8 nm, at least about 9 nm, or at least about 10 nm). Additionally or alternatively, the crystalline materials described herein can comprise crystals having an average size (diameter) distribution with substantially no sizes (diameters) above about 50 nm (e.g., above about 40 nm, above about 35 nm, above about 30 nm, above about 25 nm, above about 20 nm, or above about 15 nm). In this context of size distribution, "substantially no" should be understood to mean 3% or less, e.g., 2% or less, 1% or less, 0.5% or less, or completely no.

It should be appreciated that, with such ultra-small crystal materials, X-ray diffraction may not be fully sufficient to identify the material as having the MFI or MEL structure, in which case other analytical methods, such as high resolution transmission electron microscopy and electron diffraction, may be necessary to confirm the identity of the material as MFI and/or MEL framework type.

The MFI and/or MEL framework type crystalline materials described herein can have a composition comprising the molar relationship:

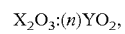

$$X_2O_3:(n)YO_2,$$

wherein X is an optional trivalent element, such as boron, aluminum, iron, and/or gallium, desirably at least including aluminum, Y is a tetravalent element, such as silicon, germanium, tin, titanium, and/or zirconium, desirably at least including silicon, and n is at least about 20, for example at least about 30 or at least about 40. In some embodiments, in which the trivalent element is present, n may be about 2000 or less, for example about 1000 or less or about 500 or less. In a particularly advantageous embodiment, n can be less than about 150, optionally in tandem with one or more minimum values of n discussed hereinabove.

In certain process embodiments of the present invention, MFI and/or MEL framework type crystalline materials, including ultra-small crystal size forms thereof, may be produced in the presence of tetrabutylammonium cations and/or tetrabutylphosphonium cations as a structure directing agent ($Q_1$). In these embodiments, a synthesis mixture can be produced containing a source of the $Q_1$ cations, such as the hydroxide and/or the halide (e.g., fluoride, chloride, bromide, and/or iodide, optionally excluding the fluoride in some embodiments), together with a source of an oxide of the tetravalent element Y, optionally a source of the trivalent element X, optionally a source of an alkali and/or alkaline earth metal (M), and water, such that the synthesis mixture has a molar composition comprising at least one, and in some embodiments both, of the following ratios: (a) $H_2O/YO_2$ molar ratio of less than about 10, for example at least about 2, such as from about 2 to about 9; and (b) $YO_2/X_2O_3$ molar ratio of less than about 150, for example at least about 20, such as from about 30 to about 140.

In some embodiments, the synthesis mixture may have an $M/YO_2$ molar ratio of 0 to less than about 0.04, for example from 0 to about 0.0125, from greater than 0 to less than about 0.04, or from greater than 0 to about 0.0125.

In particular, as will be demonstrated by the following Examples, it is found that the production of small crystal materials with high total and external surface areas can be favored when the $H_2O/YO_2$ molar ratio and/or the $M/YO_2$ molar ratio are reduced.

In addition, the synthesis mixture may have a molar composition comprising the following:

| Reactants | Useful | Exemplary |
| --- | --- | --- |
| $OH^-/YO_2$ | ~0.1 to ~0.8 | ~0.2 to ~0.5 |
| $Q_1/YO_2$ | ~0.1 to ~0.8 | ~0.2 to ~0.5 |

In other process embodiments of the present invention, MFI and/or MEL framework-type materials, including ultra-small crystal size forms thereof, may be produced in the presence of 1,5-bis(N-tributylammonium)pentane dications, and/or 1,6-bis(N-tributylammonium)hexane dications as a structure directing agent ($Q_2$). Such diquats are believed to be novel and have formulas (I) and (II) respectively:

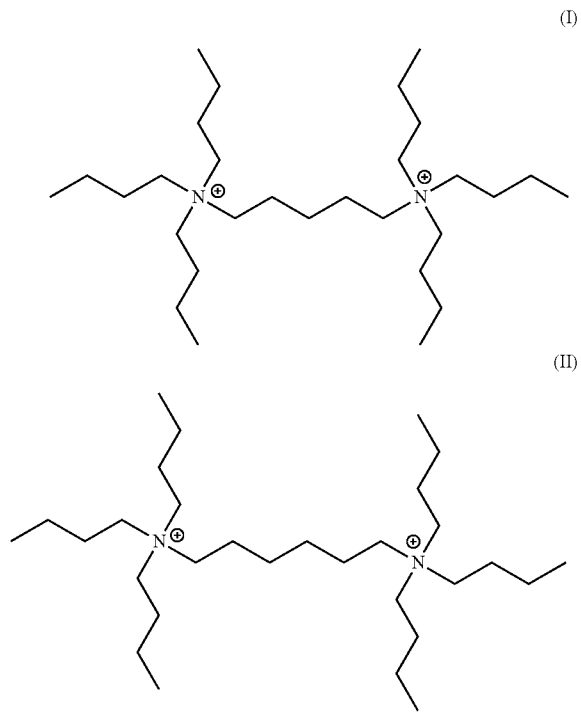

(I)

(II)

The materials of formulas (I) and (II) can readily be produced by reaction of tributylamine with 1,5-dibromopentane or 1,6-dibromohexane.

In these other process embodiments using $Q_2$ as the structure directing agent, a synthesis mixture is produced containing a source of the $Q_2$ cations, such as the hydroxide and/or the halide (e.g., fluoride, chloride, bromide, and/or iodide, optionally excluding the fluoride in some embodiments), together with a source of an oxide of the tetravalent element Y, optionally a source of the trivalent element X, optionally a source of an alkali or alkaline earth metal (M), and water such that the synthesis mixture has a molar composition comprising the following ratios:

| Reactants | Useful | Exemplary |
| --- | --- | --- |
| $YO_2/X_2O_3$ | at least ~20 | at least ~30; ~40 to <150 |
| $H_2O/YO_2$ | ~2 to ~60 | ~2 to ~50; ~2 to <10 |
| $OH^-/YO_2$ | ~0.1 to ~0.8 | ~0.2 to ~0.5 |

-continued

| Reactants | Useful | Exemplary |
| --- | --- | --- |
| $M/YO_2$ | ~0 to ~0.4 | ~0 to ~0.04 |
| $Q_2/YO_2$ | ~0.05 to ~0.4 | ~0.1 to ~0.25 |

Again, it has been unexpectedly found that the production of small crystal materials with high total and external surface areas can be favored when the $H_2O/YO_2$ molar ratio and/or the $M/YO_2$ molar ratio are reduced. Thus, in some embodiments, the $H_2O/YO_2$ mole ratio may be about 10 or less, for example about 5 or less. Additionally or alternatively, $M/YO_2$ mole ratio of the synthesis mixture may be about 0.02 or less, for example about 0.015 or less or about 0.0125 or less.

Suitable sources of the tetravalent element Y in the synthesis mixture described above can depend on the element Y selected but, in some advantageous embodiments in which Y comprises/is silicon and/or germanium, can include colloidal suspensions of silica, fumed silicas, precipitated silicas, alkali metal silicates, tetraalkyl orthosilicates, germanium oxide, or the like, or a combination thereof. If present in the synthesis mixture, the trivalent element X can normally comprise aluminum, and suitable sources of aluminum can include, inter alia, hydrated alumina and/or water-soluble aluminum salts, such as aluminum nitrate. Combined sources of aluminum and silicon may include clays and/or treated clays, such as metakaolin. Other combined sources of X and Y, including aluminosilicates such as zeolite Y, may additionally or alternatively be used.

In some embodiments, the synthesis mixture may comprise seeds of a crystalline material, such as ZSM-5 from a previous synthesis, desirably in an amount from about 0.01 wppm to about 10000 wppm, such as from about 100 wppm to about 5000 wppm, based on the weight of the synthesis mixture.

Crystallization of MFI and/or MEL framework type crystalline materials from the above synthesis mixtures can be carried out at static, tumbled, or stirred conditions in a suitable reactor vessel, e.g., polypropylene jars or Teflon™-lined or stainless steel autoclaves, at a temperature of about 80° C. to about 220° C., for example about 100° C. to about 150° C., for a time sufficient for crystallization to occur at the temperature used, e.g., from about 4 hours to about 28 days, from about 12 hours to about 21 days, or from about 1 day to about 14 days. Thereafter, the crystals can be separated from the liquid and recovered.

To the extent desired and depending on the $X_2O_3/YO_2$ molar ratio of the material, any alkali and/or alkaline earth metal cations in the as-synthesized material can be replaced in accordance with techniques well known in the art, e.g., by ion exchange with other cations. Exemplary replacing cations can include metal ions, hydrogen ions, hydrogen ion precursors (e.g., ammonium ions), or mixtures thereof. In certain embodiments, particularly preferred cations can include those with which the catalytic activity can be specifically tailored for certain hydrocarbon conversion reactions. These can include, but are not necessarily limited to, hydrogen, rare earth metals, metals of Groups 2 to 15 of the Periodic Table of the Elements, and combinations thereof. As used herein, the numbering scheme for the Periodic Table Groups is as disclosed in Chemical and Engineering News, 63(5), 27 (1985).

The as-synthesized crystalline material may further be subjected to treatment to remove all or part of the organic directing agent(s) Q1/Q2 used in its synthesis. This can be conveniently achieved/attempted by thermal treatment, for example, in which the as-synthesized material can be heated at a temperature of at least about 370° C. for at least 1 minute and generally not longer than 20 hours. While subatmospheric pressure can be employed for the thermal treatment, atmospheric and/or superatmospheric pressures can typically desired for reasons of convenience. The thermal treatment can be performed at a temperature up to about 925° C. Alternatively, the organic directing agent(s) Q1/Q2 can be removed by treatment with ozone (see, e.g., Parikh et al., Microporous and Mesoporous Materials 76 (2004) 17-22). The organic-decomposed/-free product, especially in its metal, hydrogen, and/or ammonium forms, can be particularly useful in the catalysis of certain organic (e.g., hydrocarbon) conversion reactions.

The inventive crystalline material can be intimately combined with a hydrogenating component, such as comprising molybdenum, rhenium, nickel, cobalt, chromium, manganese, and/or a noble metal (such as platinum and/or palladium), where a hydrogenation-dehydrogenation function can be desired. Such component can be in the composition by way of co-crystallization, exchanged into the composition to the extent a Group IIIA element (e.g., aluminum) is in the structure, impregnated therein, or intimately physically admixed therewith. Such component can be impregnated into/onto it such as, for example, in the case of platinum, by treating the silicate with a solution containing a platinum metal-containing ion. Thus, suitable platinum compounds for this purpose can include chloroplatinic acid, platinous chloride, and/or various compounds containing a platinum-amine complex.

The present crystalline material, when employed either as an adsorbent or as a catalyst, should be at least partially dehydrated. This can be done by heating to a temperature, e.g., in the range of 200° C. to about 370° C. in an atmosphere such as air, nitrogen, etc., and at atmospheric, subatmospheric, or superatmospheric pressures for a sufficient time, e.g., between 30 minutes and 48 hours. Dehydration can additionally or alternatively be performed at room temperature merely by placing the crystalline material in a vacuum, but a longer time may be required to obtain a sufficient amount of dehydration.

The crystalline materials described herein can be used as an adsorbent or, particularly in its aluminosilicate form, as a catalyst to facilitate one or more of a wide variety of organic compound conversion processes, including many of present commercial/industrial importance. Examples of chemical conversion processes which could be effectively catalyzed by the inventive crystalline materials can advantageously those where relatively high acid activity and large surface area can be important.

As in the case of many catalysts, it may be desirable to incorporate the inventive crystalline materials with another material resistant to the temperatures and other conditions employed in organic conversion processes. Such materials can include active and inactive materials and synthetic or naturally occurring zeolites as well as inorganic materials such as clays, silica, and/or other metal oxides such as alumina. The latter may be naturally occurring or in the form of gelatinous precipitates or gels including mixtures of silica and other metal oxides. Use of a material in conjunction with the inventive crystalline materials (i.e., combined therewith or present during synthesis of the new crystal), which are in their active form(s), can tend to change the conversion and/or selectivity of the catalyst in certain organic conversion processes. Inactive materials can suitably serve as diluents to control the amount of conversion in a given process, so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials (i.e., clays, oxides, etc.) can function as binders for the catalyst. It can be desirable to provide a catalyst having good crush strength, because, in commercial use, it can be particularly desirable to prevent the catalyst from attrition into powder-like materials. These clay and/or oxide binders have been employed normally primarily for the purpose of improving the crush strength of the catalyst.

Naturally occurring clays that can be composited with the inventive crystalline materials can include the montmorillonite and kaolin family, which families include the subbentonites, and the kaolins commonly known as Dixie, McNamee, Ga., and Florida clays or others in which the main mineral constituent is halloysite, kaolinite, dickite, nacrite, or anauxite. Such clays can be used in the raw state as originally mined or initially subjected to calcination, acid treatment, or chemical modification. Other useful binders can include inorganic oxides, such as silica, zirconia, titania, magnesia, beryllia, alumina, and mixtures thereof.

In addition to the foregoing materials, the inventive crystalline materials can be composited with a porous matrix material such as silica-alumina, silica-magnesia, silica-zirconia, silica-thoria, silica-beryllia, silica-titania, or ternary compositions such as silica-alumina-thoria, silica-alumina-zirconia silica-alumina-magnesia, and silica-magnesia-zirconia.

The relative proportions of MFI and/or MEL framework-type crystalline material and inorganic oxide matrix may vary widely, with the sieve content ranging from about 1 wt % to about 90 wt % and more usually, particularly when the composite is prepared in the form of beads, in the range from about 2 wt % to about 80 wt % of the composite.

Additionally or alternatively, the invention can include one or more of the following embodiments.

Embodiment 1

A process for producing a crystalline material having the MFI and/or MEL framework-type, the process comprising: (i) preparing a synthesis mixture capable of forming the crystalline material, the mixture comprising a source of an oxide of a tetravalent element Y, optionally a source of a trivalent element X, optionally a source of an alkali and/or alkaline earth metal (M), water, and a directing agent ($Q_1$) comprising tetrabutylammonium cations and/or tetrabutylphosphonium cations, wherein the synthesis mixture has a composition comprising at least one of: (a) $H_2O/YO_2$ molar ratio of about 10 or less (for example about 5 or less); and (b) $YO_2/X_2O_3$ molar ratio of less than about 150; (ii) heating the mixture under crystallization conditions including a temperature from about 80° C. to about 220° C. and a time from about 4 hours to about 28 days until crystals of the crystalline material are formed; and (iii) recovering the crystalline material from step (ii).

Embodiment 2

A process for producing a crystalline material having the MFI and/or MEL framework-type, the process comprising: (i) preparing a synthesis mixture capable of forming said crystalline material, said mixture comprising a source of an oxide of a tetravalent element Y, optionally a source of a trivalent element X, optionally a source of an alkali and/or alkaline earth metal (M), water, and a directing agent (Q₂) comprising 1,5-bis(N-tributylammonium)pentane dications, and/or 1,6-bis(N-tributylammonium)hexane dications; (ii) heating the mixture under crystallization conditions including a temperature of from about 80° C. to about 220° C. and a time from about 4 hours to about 28 days until crystals of the crystalline material are formed; and (iii) recovering the crystalline material from step (ii).

Embodiment 3

The process of embodiment 1 or embodiment 2, wherein X includes one or more of B, Al, Fe, and Ga, and Y includes one or more of Si, Ge, Sn, Ti, and Zr.

Embodiment 4

The process of any of the preceding embodiments, wherein X includes aluminum, and Y includes silicon.

Embodiment 5

The process of any one of the preceding embodiments, wherein the synthesis mixture has a $YO_2/X_2O_3$ mole ratio of at least about 20.

Embodiment 6

The process of any one of the preceding embodiments, wherein the $H_2O/YO_2$ mole ratio of the synthesis mixture is at least about 2, for example about 2 to about 9.

Embodiment 7

The process of any one of the preceding embodiments, wherein $M/YO_2$ mole ratio of the synthesis mixture is about 0.04 or less, for example about 0.02 or less or about 0.0125 or less.

Embodiment 8

The process of any one of the preceding embodiments, wherein the crystallization conditions include a temperature from about 100° C. to 150° C.

Embodiment 9

The process of any one of the preceding embodiments, wherein the crystalline material recovered in (iii) has a total surface area (as determined by the t-plot method for nitrogen physisorption) of at least about 750 m²/g and/or an external surface area (as determined by the t-plot method for nitrogen physisorption) of at least about 350 m²/g, Embodiment 10

The process of any one of embodiments 2-9, wherein the synthesis mixture has a composition, in terms of mole ratios, within the following ranges: $YO_2/X_2O_3$ of at least about 20; $H_2O/YO_2$ of about 2 to about 60 (for example, about 10 or less or about 5 or less); $OH^-/YO_2$ of about 0.1 to about 0.8; $M/YO_2$ of 0 to about 0.4; and $Q_2/YO_2$ of about 0.05 to about 0.4.

Embodiment 11

The process of any one of the preceding embodiments, wherein the crystalline material recovered in (iii) has: (a) an average size (diameter) of about 35 nm or less (e.g., about 30 nm or less, about 25 nm or less, about 20 nm or less, about 15 nm or less, or about 10 nm or less) and optionally at least about 3 nm (e.g., at least about 4 nm, at least about 5 nm, at least about 6 nm, at least about 7 nm, at least about 8 nm, at least about 9 nm, or at least about 10 nm); and/or (b) an average size (diameter) distribution with substantially no sizes (diameters) above about 50 nm (e.g., above about 40 nm, above about 35 nm, above about 30 nm, above about 25 nm, above about 20 nm, or above about 15 nm).

Embodiment 12

A crystalline material having the MFI and/or MEL framework-type produced by the process of one or more of the preceding embodiments.

Embodiment 13

A crystalline material, such as having an MFI and/or MEL framework-type, having within its pore structure 1,5-bis(N-tributylammonium) pentane dications, and/or 1,6-bis(N-tributylammonium)hexane dications.

Embodiment 14

A crystalline material having the MFI and/or MEL framework-type and a chemical composition comprising the molar relationship: $(n)YO_2:X_2O_3$, wherein n is a number of at least about 20 and less than about 2000, X is a trivalent element and Y is a tetravalent element and wherein the crystalline material comprises crystals having a total surface area (as determined by the t-plot method for nitrogen physisorption) in excess of about 770 m²/g and/or an external surface area (as determined by the t-plot method for nitrogen physisorption) in excess of about 400 m²/g.

Embodiment 15

An organic nitrogen compound comprising a dication having formula (I) or (II):

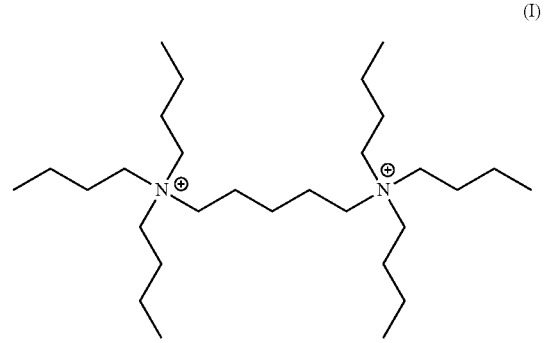

-continued (II)

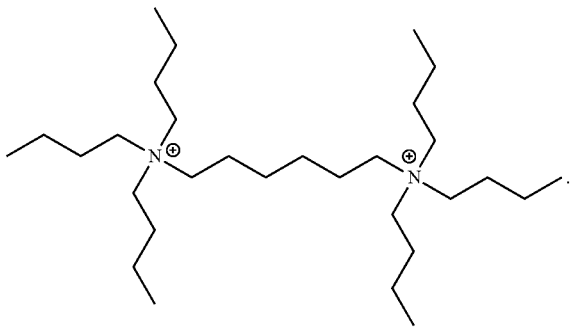

EXAMPLES

The invention will now be more particularly described with reference to the following Examples and the accompanying drawings.

Example 1

An MFI synthesis similar to that reported by Zhang et al. (*Science*, 336 (2012), 1684-1687; discussed above) was conducted using tetrabutylphosphonium hydroxide (TBPOH) as the structure directing agent (SDA) and with a molar gel composition of ~0.30 TBPOH: ~0.0125NaOH: ~0.005 $Al_2O_3$: ~1 $SiO_2$: ~10 $H_2O$: ~4EtOH. The presence of ethanol in this synthesis came from the use of tetraethylorthosilicate (TEOS) as the silica source—once hydrolyzed in water, each TEOS can produce approximately four molecules of ethanol. The alumina source was aluminum sulfate. After ~4 days of heating under tumbling conditions at ~115° C., this synthesis yielded a product with a very high total surface area of ~620 $m^2/g$ and an external surface area of ~317 $m^2/g$. These high surface areas appear to be consistent with those expected for materials with very small crystals.

Figure 2:
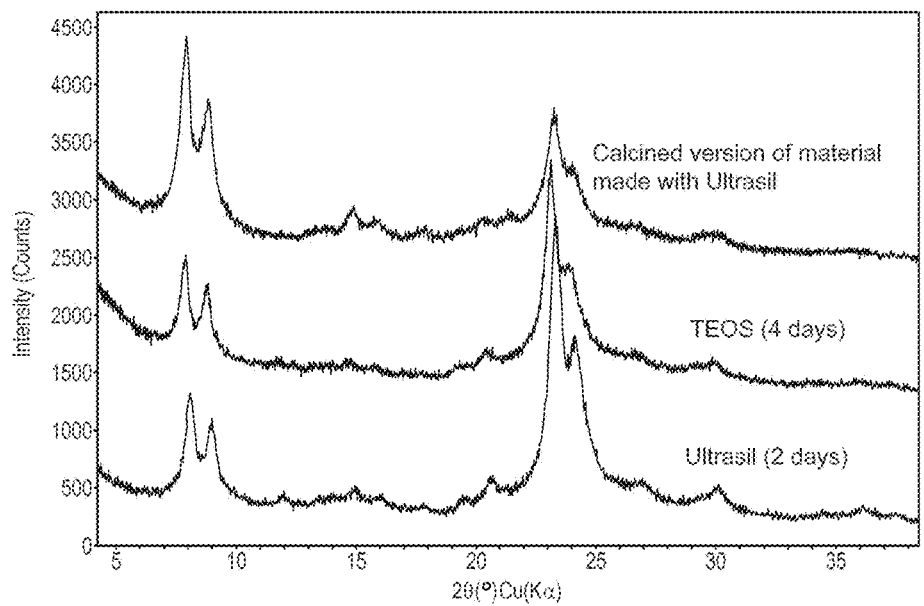
FIG. 2 compares the X-ray diffraction (XRD) pattern of the as-synthesized material of Example 1 with those of the as-synthesized and calcined products of Example 2.
Figure 3:
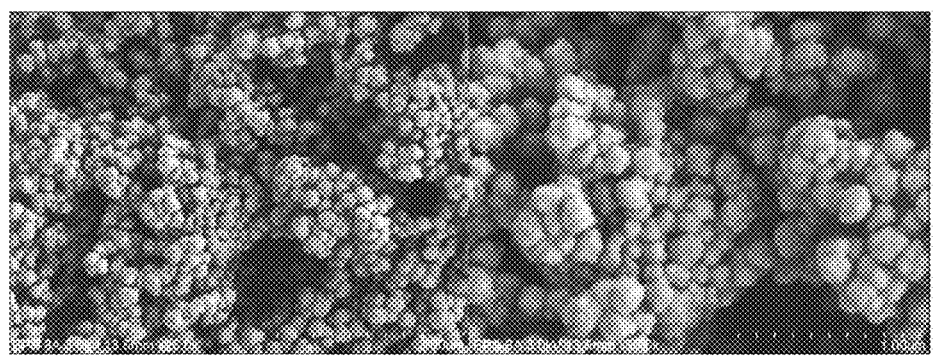
FIG. 3 shows scanning electron microscope (SEM) images of the product of Example 1.
Figure 4:
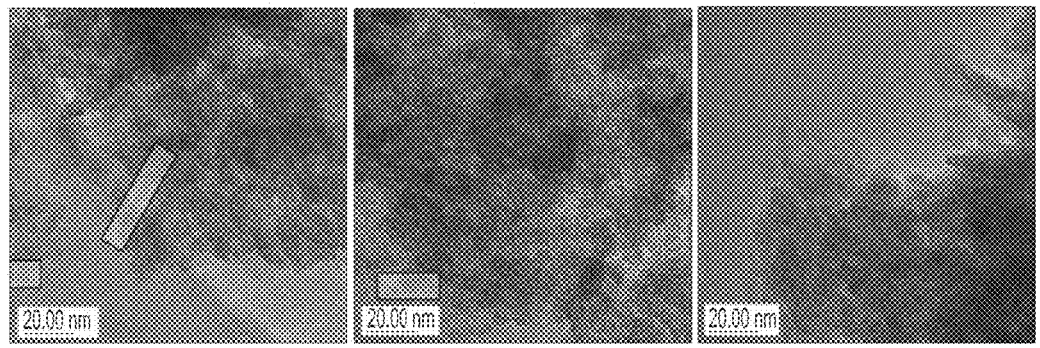
FIG. 4 shows high-resolution transmission electron microscope (HRTEM) images of the product of Example 1.

The powder XRD pattern of the as-synthesized product of Example 1 is shown in FIG. 2, with SEM images of the product shown in FIG. 3. At the magnification of the SEM, no faceted domains seem to be discernible. FIG. 4 shows HRTEM images of the same material. Several images were collected on different areas of the product, and no amorphous domains were observed. Unlike the products reported by Zhang et al., the products here do not appear to exhibit an orderly "self-pillared" arrangement. However, there are many small crystals that are overlapping and arranged at different orientations relative to one another. The thicknesses of the various crystals do not appear to be uniform. In a few cases, crystals that appear ~1-2 units cell in thickness can be discerned—these are surrounded by transparent boxes. The fringes within these crystals appear to have characteristics of MFI and/or MEL materials. In the middle image, the pores of the MFI framework-type can be seen—the distance between the pores matches those in other MFI and/or MEL materials.

Example 2

The synthesis of Example 1 was repeated using Ultrasil™ precipitated silica in place of TEOS and tetrabutylammonium hydroxide (TBAOH) as the structure directing agent (SDA). The molar composition of the gel was ~0.30 TBAOH: ~0.010NaOH: ~0.005 $Al_2O_3$: ~1 $SiO_2$: ~10 $H_2O$. No ethanol was added for this preparation. In this case, the synthesis appeared to be complete after ~2 days of heating at ~115° C. Without being bound by theory, although this synthesis used a different SDA and a different silica source, the faster crystallization time could be due to the absence of the ethanol rather than to the different nature of the silica sources. The total surface area of this material was ~760 $m^2/g$ and the external surface area was ~370 $m^2/g$. The total surface area was notably greater than the 710 $m^2/g$ measured for the unilamellar preparations by Ryoo et al. (*Nature* 461, 246-249; discussed herein) and is believed to be one of the highest surface areas reported for any MFI-type material.

FIG. 2 compares the powder XRD patterns of the products of Examples 1 and 2 and appears to show in each broad features characteristic of materials with very small crystals. After calcination, shown in FIG. 2 for the product of Example 2, there appeared to be increases in the relative intensities of the low-angle features often observed in microporous materials. One apparent consequence of the small crystal dimensions can be that many of the distinct peaks from a "normal" ZSM-5 appeared as shoulders or formed broad bumps with their neighboring peaks. Notably, the valley between the first low-angle peaks possesses an intensity greater than half the intensity of the peak around 8.9° two-theta.

Example 3

The synthesis of Example 1 was repeated in ~23-mL and ~45-mL tumbled autoclaves, using TEOS as the silica source and aluminum isopropoxide as the aluminum source. The molar composition of the gel was ~0.30 TBPOH: ~0.0125NaOH: ~0.0125 $Al_2O_3$: ~1 $SiO_2$: ~10 $H_2O$: ~4EtOH. Because more aluminous preparations of ZSM-5 can generally require more time than those with higher Si/Al ratios, a higher temperature of ~160° C. was employed. After ~8 days of heating, and subsequent calcination at ~600° C., a product with ~640 $m^2/g$ total BET surface area and an external surface area of ~381 $m^2/g$ was obtained. When the product was analyzed in its uncalcined form, the same external surface area was measured, but no micropore volume was observed (presumably because the SDA remained within the micropores).

Example 4

The synthesis of Example 3 was repeated on a larger scale in a ~300-mL, overhead-stirred autoclave. After ~8 days of heating, a product with only ~419 $m^2/g$ total BET and ~44 $m^2/g$ external surface area was obtained. These numbers are more representative of typical samples of ZSM-5. The features in the powder pattern of this material were much sharper than those of the material prepared from the tumbled reactors. Without being bound by theory, although a definitive explanation for the variation in crystal sizes is not currently available, the surface areas of products from the overhead-stirred systems can frequently appear lower than in tumbled systems.

Examples 5 and 6

The syntheses of Examples 3 and 4 were repeated but using aluminum sulfate and Ultrasil™ as the aluminum and silica sources, respectively, under otherwise identical conditions. After ~6 days of heating under tumbled conditions, a product with ~568 $m^2/g$ total and ~191 $m^2/g$ external surface area was obtained. When the synthesis was repeated in a ~300-mL, overhead-stirred autoclave, the total and external surface areas were reduced to ~510 m$^2$/g and ~129 m$^2$/g (510/129), respectively. Again, the overhead-stirred system appeared to yield a product with lower surface area, but the differences were not as notable as observed in the system of Examples 3 and 4, utilizing TEOS and aluminum isopropoxide.

Example 7

Figure 5:
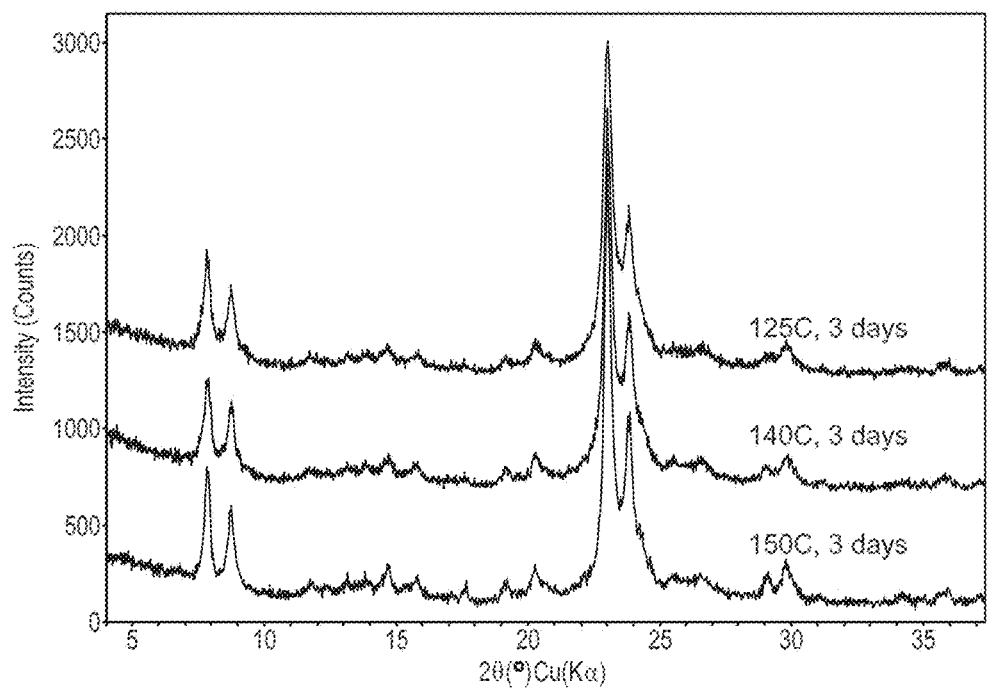
FIG. 5 compares the XRD patterns obtained when the synthesis of Example 7 was repeated at varying temperatures between ~125° C. and ~150° C.

A series of experiments were performed at different temperatures at a SiO$_2$/Al$_2$O$_3$ molar ratio of ~100 in the aluminum sulfate/Ultrasil™ system. Each synthesis was carried out in a ~300-mL overhead stirred autoclave using TBPOH as the SDA and involving an H$_2$O/SiO$_2$ molar ratio of ~10. After ~4 days of heating at ~160° C., the product appeared to possess a relatively sharp powder XRD pattern. When the synthesis was repeated at ~150° C. for ~3 days, the product had total/external surface areas of ~503/~103 m$^2$/g. At ~140° C. for ~3 days, the total/external surface areas increased to ~538/~169 m$^2$/g. At ~125° C. for ~3 days, the corresponding numbers were ~534/~196 m$^2$/g. Thus, the decrease in temperature from ~140° C. to ~125° C. did not appear to produce much change in the total measured BET surface areas, but the contribution of the external surface area appeared enhanced. FIG. 5 shows the broadening that occurred in the features of the powder XRD patterns of the products obtained, as synthesis temperature was decreased.

Example 8

A series of experiments similar to Example 7 were conducted but with the gel compositions having a SiO$_2$/Al$_2$O$_3$ molar ratio of ~50. The first experiment in a ~300-mL autoclave at ~160° C. for ~6 days gave a product with total/external surface areas of ~514/~155 m$^2$/g. When the experiment was repeated but only heated for ~4 days, the surface area numbers increased to ~551/~192 m$^2$/g. In a ~23-mL tumbled autoclave heated at ~150° C. for ~5 days, the numbers increased further to ~592/~228 m$^2$/g. Another synthesis was performed in a ~300-mL overhead-stirred autoclave with a staged heating sequence in which the gel was heated at ~140° C. for ~2 days and then ~150° C. for ~3 more days. In that case, the total/external surface areas were ~548/~205 m$^2$/g, which was about the same as the product obtained from ~4 days of heating at ~160° C.

Example 9

When the experiments of Example 8 were repeated in tumbled ~125-mL reactors, there appeared to be a clear trend in the observed total/external surface areas: at ~140° C. for ~4 days, the resulting surface areas were ~496/~130 m$^2$/g; at ~130° C. for ~4 days, the resulting surface areas were ~538/~206 m$^2$/g; and at ~120° C. for ~6 days, the resulting surface areas were ~559/~298 m$^2$/g.

Example 10

The experiments of Example 8 were again repeated, but with lower SiO$_2$/Al$_2$O$_3$ molar ratios of ~40 and ~30. The experiment with SiO$_2$/Al$_2$O$_3$ molar ratio of ~40 employed TEOS and aluminum isopropoxide. The experiment with SiO$_2$/Al$_2$O$_3$ molar ratio of ~30 employed Ultrasil™ and aluminum sulfate. After heating for at least ~40 days at ~170° C. and ~160° C., respectively, both experiments appeared to produce only amorphous phases. It was noted that the lower Si/Al ratios of the gel and in any resultant product typically correlate with a need for a higher concentration of sodium to assist in crystallization. The Na/SiO$_2$ molar ratio of the gels in these experiments remained low at ~0.0125.

When the experiments were repeated with gel SiO$_2$/Al$_2$O$_3$ molar ratio of ~32 and an increased Na/SiO$_2$ molar ratio of ~0.05, relatively sharp, fully crystalline ZSM-5 products were obtained after only ~3 days of heating at both ~160° C. and ~140° C. Even at ~125° C., a relatively sharp ZSM-5 product was observed. Introducing extra sodium into the system can allow a more aluminous product to form, but the increased sodium level can also promote the formation of larger crystallites. Hence, in such systems where very small crystals are desired, it can be important to reduce and/or minimize the concentration of sodium, to prevent the formation of larger crystals.

Example 11

A series of experiments were conducted at the ~23-mL scale with TBAOH as the SDA under concentrated conditions (H$_2$O/Si ratio 3). To obtain these low MO/Si ratios, water was removed from the ~40% TBAOH solution using a rotary evaporator at ~70° C. to obtain a ~70% TBAOH solution (~2.7 mmol/g). Typically, concentrating an SDA solution under elevated temperatures is not desirable, as it can lead to Hofmann elimination. In this case, although there was discoloration of the gel after the removal of the water, no degradation was observable by NMR analysis. Zeolite synthesis with a gel SiO$_2$/Al$_2$O$_3$ molar ratio of ~50 at ~150° C. for ~5 days yielded a product with total/external surface areas of ~523/~237 m$^2$/g. A similar preparation with an SiO$_2$/Al$_2$O$_3$ molar ratio of ~64 at ~140° C. for ~4 days yielded a product with total/external surface areas of ~533/~219 m$^2$/g.

Example 12

A series of experiments were conducted using 1,5-bis(N-tributyl-ammonium)pentane hydroxide as the SDA. This C5-diquat was produced by adding 17.74 g tributylamine to ~60 mL acetonitrile, followed by addition of ~10.0 g of 1,5-dibromopentane. The mixture was then heated for ~4 days at ~80° C. inside of a sealed Teflon™ container. The product was then isolated by rotary evaporation of the solvent, rinsing the oil with ether, decanting the ether, and then rotary evaporating under vacuum (reduced pressure) at ~80° C. until solids appeared to form. The solids were then slurried in an acetone/ether mixture, isolated by filtration, and allowed to dry. The purity of the product was verified by $^1$H and $^{13}$C NMR. The solid was then exchanged into its hydroxide form using Dowex™ exchange resin.

The resultant SDA solution was concentrated by rotary evaporation to about 60% by mass and was then used to prepare a gel having a molar composition of ~0.30 C5-Diquat: ~0.0125NaOH: ~0.02 Al$_2$O$_3$: ~1 SiO$_2$: ~3.5 H$_2$O. After ~9 days of heating at ~160° C., the gel yielded a product with total/external surface areas of ~548/~203 m$^2$/g. When the experiment was repeated with the H$_2$O/SiO$_2$ ratio increased to ~10, the product obtained after ~9 days of heating at ~160° C. had total/external surface areas of ~589/~222 m$^2$/g. In another experiment, another portion of the gel with the H$_2$O/SiO$_2$ ratio of ~10 was heated at ~150° C. for ~21 days and yielded a product with total/external surface areas of ~539/~205 m$^2$/g.

In certain experiments, the C5-diquat SDA appeared to need more time and/or higher temperatures to provide similar structural products than for the TBAOH SDA.

Example 13

A series of experiments similar to those of Example 12 were conducted but using 1,6-bis(N-tributylammonium) pentane hydroxide as the SDA. This C6-diquat was produced in the same way as the C5-diquat but by substituting 1,6-dibromohexane for the 1,5-dibromopentane. Again the resultant SDA solution was concentrated by rotary evaporation to about 60% by mass before being used in the synthesis reactions below.

The first syntheses with the C6-diquat were done at ~150° C. for ~7 days. At an $H_2O/SiO_2$ ratio of ~10, the product had total/external surface areas of ~512/~241 m$^2$/g, and, at an $H_2O/SiO_2$ ratio of ~3.5, the product had total/external surface areas of ~577/~269 m$^2$/g. When the synthesis at the $H_2O/SiO_2$ ratio of ~3.5 was repeated at ~135° C. for ~8 days, the total/external surface areas were ~548/~269 m$^2$/g. Next, the syntheses were repeated with $H_2O/SiO_2$ ratios of ~3.5 at ~125° C. and ~115° C. using seeds. After ~4 days of heating at ~125° C., the product had measured total/external surface areas of ~575/~289 m$^2$/g, and, after ~4 days of heating at ~115° C., the product had measured total/external surface areas of ~594/~346 m$^2$/g.

Without being bound by theory, the significantly reduced crystallization times with the C6-diquat, as compared with the C5-diquat, suggest that the distances between the N centers of the C6 diquat may be a good match to that distance between the intersections of the product framework-type structure. Moreover, although the crystallization can be accomplished quicker, the ability to produce materials with small crystals appeared to have been retained.

Example 14

The products of the preparations in highly concentrated media have typically been isolated by centrifugation, followed by washing, because the particles are typically filtered through the fritted funnels. An experiment was therefore conducted to test whether the centrifugation/washing steps could be avoided by simply drying the crystallized gel and then calcining the entire product (to remove the SDA). Such a simplified finishing process could be advantageous for larger scale production. One potential concern for such a streamlined process is that excess alkali cations could degrade the zeolite during calcination, if they function as basic species. However, this was unlikely to occur in the inventive syntheses, which were run at relatively low sodium/Si ratios. Another potential concern for such a streamlined process is that, in most systems, a non-trivial amount of silica generally remains dissolved in solution—calcination of such a dried product with could likely result in amorphous material or in other undesirable high-silica phases/diluents. However, this too was unlikely to occur in the inventive syntheses, because, in relatively low water-to-silica systems, there is little excess water, and much of what excess water exists is typically bound to the surface are of the very small crystallite products, causing the yields in these concentrated systems to be relatively high (close to 100%, or at least >90%).

Figure 6:
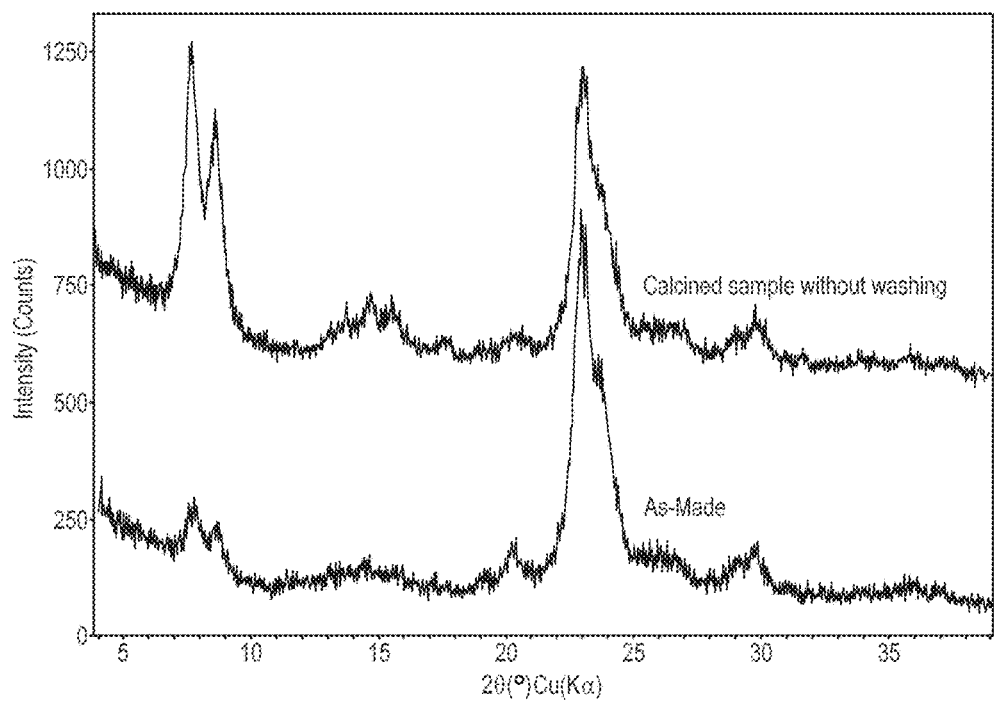
FIG. 6 compares the XRD patterns of the Example 14 product (a) after synthesis and without washing and (b) after calcination.
Figure 7:
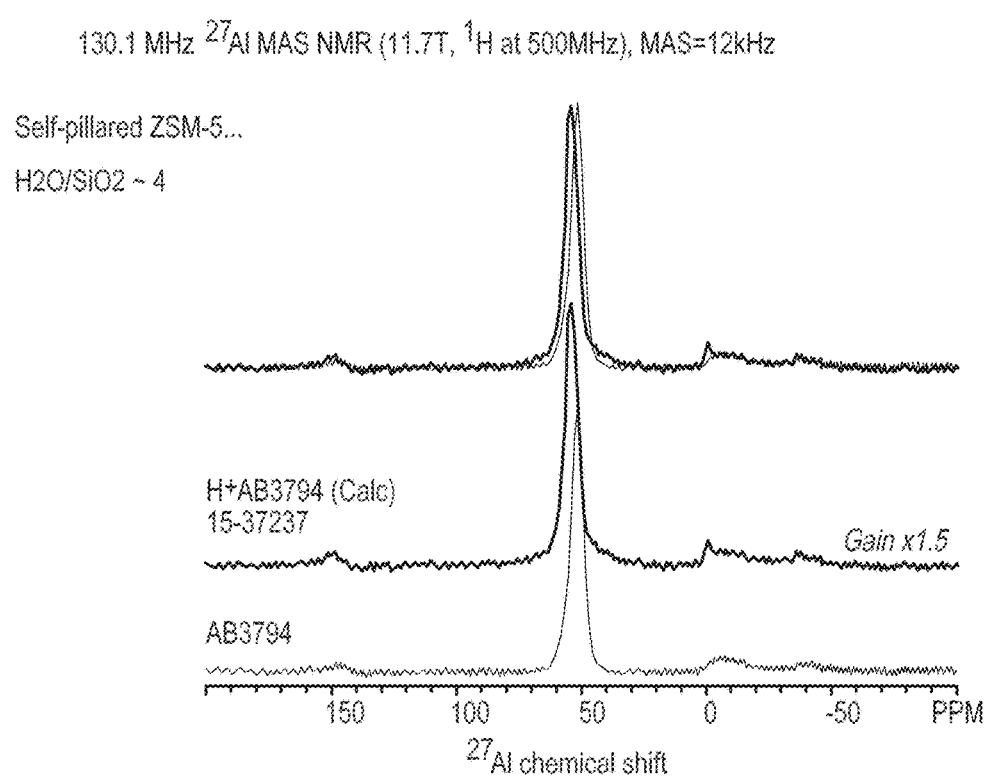
FIG. 7 shows the $^{27}Al$ NMR spectra of the as-made product of Example 14 isolated without any washing step (bottom), the calcined version of that product (middle), and the two spectra superimposed (top).

Thus, a portion of the as-synthesized product of Example 13 generated at ~135° C. for ~8 days was run without washing the product. The XRD spectrum of this product is shown in the lower portion of FIG. 6. The unwashed product was then calcined to ~600° C. and again analyzed by XRD. The resultant pattern is shown in the top portion of FIG. 5, and no significant amorphitization of the product was observed. FIG. 7 shows the $^{27}$Al NMR before and after calcination of the product to ~600° C. to remove the SDA. Before calcination, all of the aluminum can be in a tetrahedral environment. Surprisingly, after calcination, ion-exchange, and subsequent re-calcination, only about 3-4% of the aluminum becomes octahedral. Contrarily, in typical ZSM-5 materials, at least 10% of the aluminum becomes octahedral after calcination.

Example 15

The process of Example 13 with the C6-diquat was repeated at a gel $SiO_2/Al_2O_3$ molar ratio of ~60 and a $H_2O/SiO_2$ molar ratio of ~3.5 without the addition of any sodium and in the presence of ~5 wt % ZSM-5 seeds. After about five days of heating at ~135° C., a crystalline product was obtained with total/external surface areas of ~623/~337 m$^2$/g. By not using sodium in this synthesis, the product could be directly calcined, without requiring either a prior or a subsequent ion-exchange to convert the zeolite to its fully acidic form.

Examples 16 and 17

Figure 8:
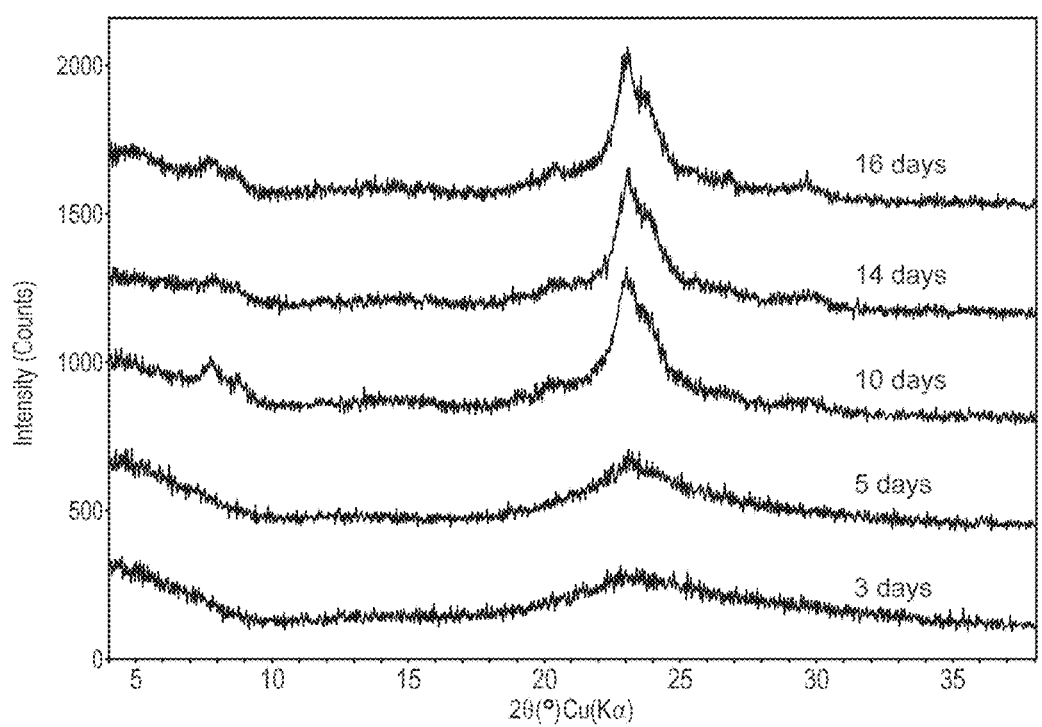
FIG. 8 shows XRD patterns of products of Example 16 taken after different heating periods at ~100° C.
Figure 9:
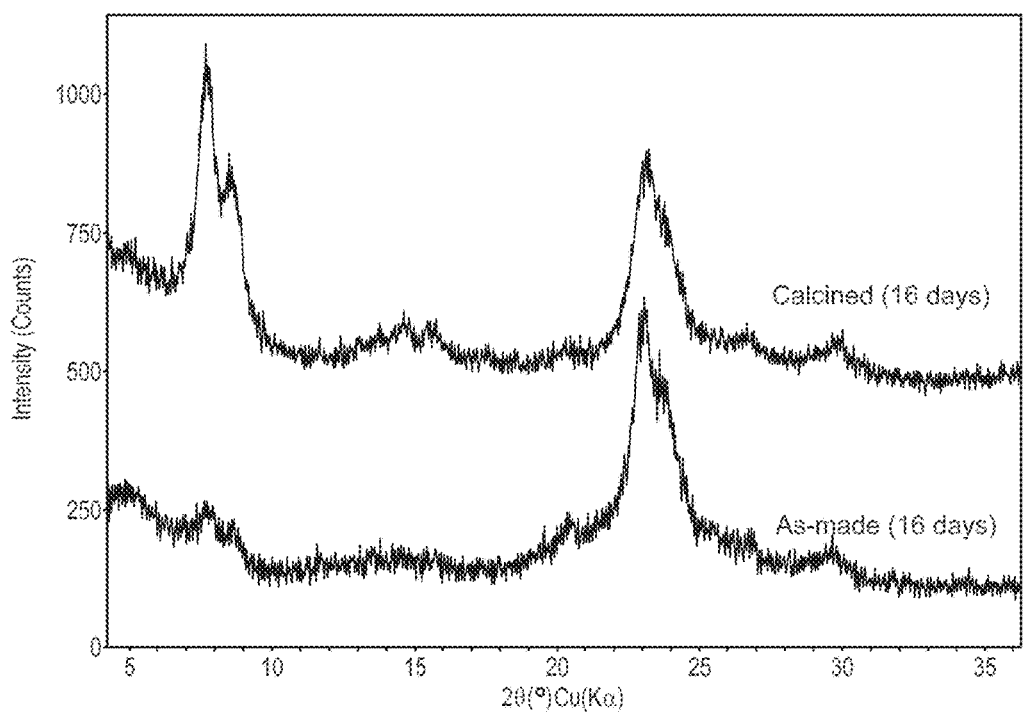
FIG. 9 compares the XRD patterns of the as-made and calcined products of Example 16 obtained after ~16 days of heating at ~100° C.
Figure 10:
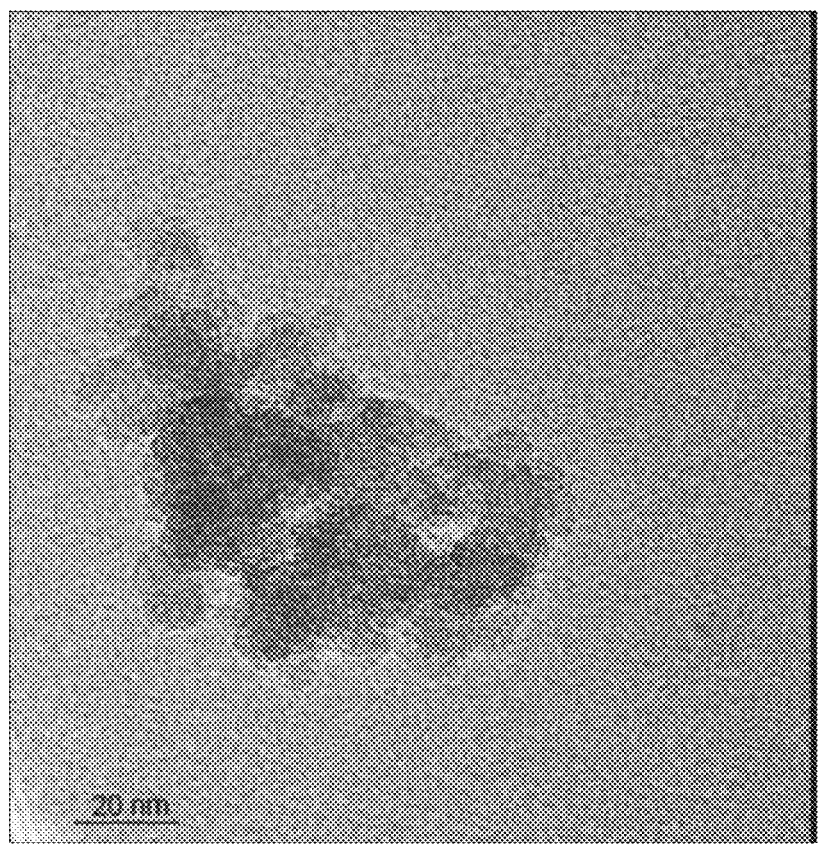
FIG. 10 shows TEM images of the calcined product of Example 16 obtained after ~16 days of heating at ~100° C.
Figure 11:
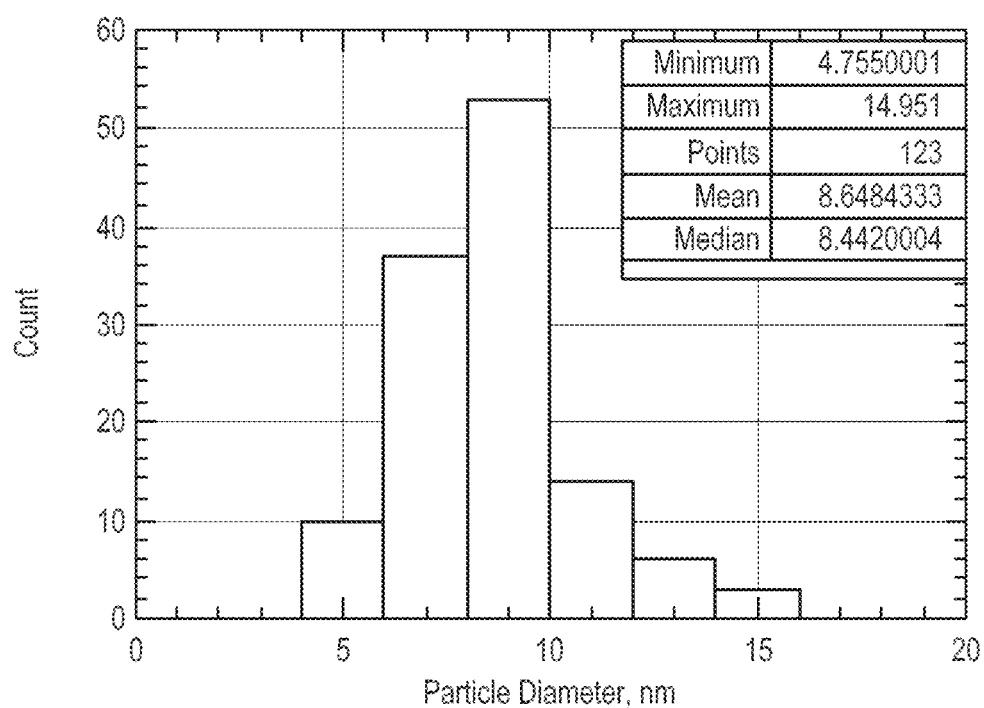
FIG. 11 shows a bar graph of the crystal size distribution of the calcined product of Example 16 obtained after ~16 days of heating at 100° C.

The process of Example 15 was repeated with $SiO_2/Al_2O_3$ molar ratios of ~80 (Example 16) and ~150 (Example 17) at a temperature of ~100° C. After heating for ~16 and ~12 days, respectively, products were obtained with total/external surface areas of ~861/~550 m$^2$/g and ~757/~409 m$^2$/g. Decreasing the temperature appeared to result in a large increase in surface area of the product, but more time appeared to be required for the crystallization. FIG. 8 shows powder XRD patterns of the products of Example 16 taken after different heating periods. Between ~10 and ~16 days, there appeared only a slight sharpening of the mid-angle features, indicating that the synthesis may have been complete at ~10 days. FIG. 9 shows a comparison of the XRD patterns of the as-made and calcined products of Example 16 obtained after ~16 days of heating at ~100° C. FIG. 10 shows TEM images of the calcined product of Example 16 obtained after ~16 days of heating at ~100° C., and FIG. 11 shows a bar graph of the crystal size distribution. Because the crystals are believed to be in the form of thin plates, these distributions may represent only the larger crystal dimensions (diameters). The distribution in FIG. 11 represents crystal size measurements made by TEM in transmission mode. Random areas of each TEM grid/holder containing the sample were used. The number of random areas can be varied, based on the number of resolvable particles in any given area, such that at least 100 particles can be measured in all areas for each sample. To eliminate any bias, it is best practice to use at least 3 random areas. For each particle under visual inspection, the appropriate magnification was used to capture an average dimension (diameter) for each resolvable particle. The mean of the size distribution of all measured particles was used herein to represent the "average" crystal dimension (diameter).

Examples 18 and 19

Figure 12:
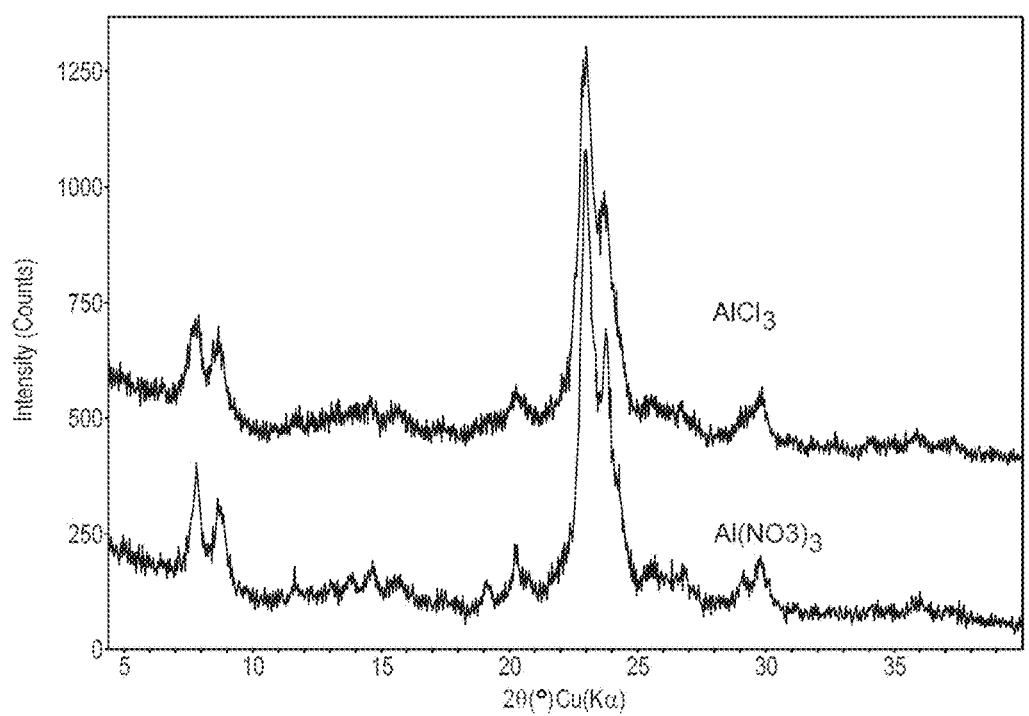
FIG. 12 compares the XRD patterns of the products of Example 18 (using aluminum chloride as the aluminum source) and Example 19 (using aluminum nitrate as the aluminum source).

The results of Examples 15-17 demonstrated that even relatively small concentrations of sodium can have dramatic effects on the crystallization time and on the final product morphologies. To investigate the potential influence of the anion associated with the aluminum source, two otherwise identical syntheses were conducted, one using aluminum chloride (Example 18) as the aluminum source and the other using aluminum nitrate (Example 19). In each case, the synthesis gel employed the C6-diquat of Example 13 and had the following molar composition: ~1SiO$_2$: ~0.04Al$^{+3}$: ~3.5 H$_2$O: ~0.15 SDA(OH)$_2$: ~0.0125NaOH. Each synthesis was carried out in a new Teflon™ liner, to avoid the potential influence of different concentrations of sodium from used liners (which are typically cleaned in sodium hydroxide after each use). Both syntheses were placed inside the same oven at the same time under tumbling conditions and then removed after heating for the same period of time (~4 days at ~150° C.). FIG. 12 compares the XRD powder patterns of the products. The spectrum of the product from the synthesis with aluminum chloride appeared to have somewhat broader peaks than that prepared from aluminum nitrate. Its total surface area was negligibly higher (~530 vs ~512 m$^2$/g), but its external surface area was almost 50 m$^2$/g higher. These isolated results suggest that the nature and concentration of the anions in the synthesis also have an influence on the morphologies of their respective products.

Example 20

The process of Example 13 was repeated with the C6-diquat/SiO$_2$ molar ratio reduced from ~0.3 to ~0.14 and the H$_2$O/SiO$_2$ molar ratio increased to ~5.5-6. In addition, Alcoa C-31™ aluminum (aluminum trihydrate) was used as the aluminum source. After heating for ~8 days at ~150° C., a product was obtained with total/external surface areas of ~540/~240 m$^2$/g.

Example 21

A series of experiments similar to those of Example 12 were conducted but using 1,4-bis(N-tributylammonium)butane hydroxide as the SDA. This C4-diquat was produced in the same way as the C5-diquat but by substituting 1,4-dibromobutane for 1,5-dibromopentane.

The C4 diquat preparations did not appear to produce any crystalline phases after several weeks of heating at ~160° C. under H$_2$O/Si ratios of ~3.5 and ~10.

Examples 22 and 23

Figure 13:
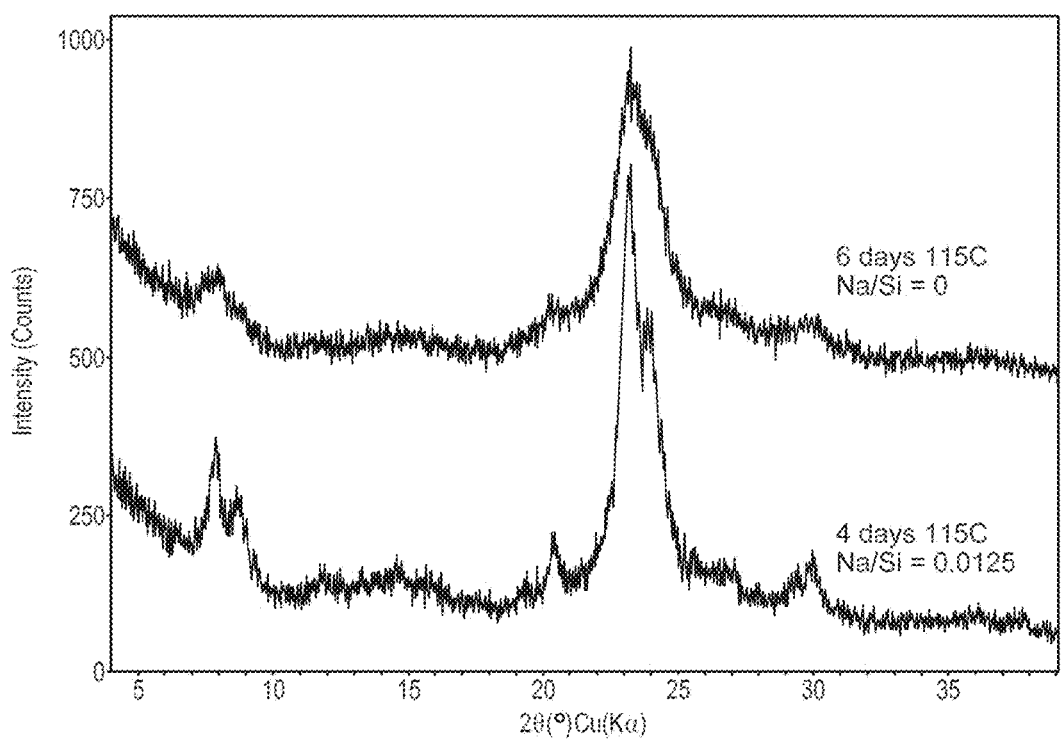
FIG. 13 compares the XRD patterns of the products of Examples 22 and 23.

A series of borosilicate analogues of the materials produced in the preceding Examples were produced using boric acid as the boron source and the C6 diquat of Example 13 as the SDA. The first synthesis (Example 22) used an Na/SiO$_2$ ratio of ~0.0125 and was conducted at ~115° C. for ~4 days. After the product was calcined, it possessed a total/external surface area of ~319/~175 m$^2$/g. Without being bound by theory, it was speculated that this lower-than-expected surface area could be due to the sodium in the synthesis and subsequent product. When the synthesis was repeated with no alkali cations (Example 23), with heating at ~115° C. for ~6 days, the surface areas increased to ~665/~483 m$^2$/g. FIG. 13 shows the powder XRD patterns of the as-made products of each of these preparations. As was observed previously in the aluminosilicate systems, the absence of sodium appeared to implicate longer crystallization times, but its absence also appeared to produce products with broader powder diffraction peaks (indicating much smaller crystals).

Examples 24 and 25

The preparations of Examples 16 and 17 were repeated using TBAOH rather than the C6 diquat as the SDA. After ~13 days at ~100° C., the synthesis mixture with a SiO$_2$/Al$_2$O$_3$ molar ratio of ~80 (Example 24) yielded a product with a total/external surface area of ~846/~518 m$^2$/g, while, after ~11 days at ~100° C., the synthesis mixture with a SiO$_2$/Al$_2$O$_3$ molar ratio of ~150 (Example 25) yielded a product with a total/external surface area of ~821/~489 m$^2$/g.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing a crystalline material having the MFI and/or MEL framework-type, the process comprising:
    (i) preparing a synthesis mixture capable of forming the crystalline material, the mixture comprising a source of an oxide of a tetravalent element Y, a source of a trivalent element X, a source of an alkali or alkaline earth metal (M), water, and a directing agent (Q$_1$) comprising tetrabutylammonium cations, and/or tetrabutylphosphonium cations, wherein the synthesis mixture has a composition comprising:
        (a) H$_2$O/YO$_2$ molar ratio of about 10 or less;
        (b) YO$_2$/X$_2$O$_3$ molar ratio of less than about 150; and
        (c) M/YO$_2$ molar ratio of about 0.04 or less;
    (ii) heating the mixture under crystallization conditions including a temperature from about 80° C. to about 220° C. and a time from about 4 hours to about 28 days until crystals of the crystalline material are formed; and
    (iii) recovering the crystalline material from step (ii).

2. The process of claim 1, wherein X includes one or more of B, Al, Fe, and Ga, and Y includes one or more of Si, Ge, Sn, Ti, and Zr.

3. The process of claim 1, wherein X includes aluminum, and Y includes silicon.

4. The process of claim 1, wherein the synthesis mixture has a YO$_2$/X$_2$O$_3$ mole ratio of at least about 20.

5. The process of claim 1, wherein the H$_2$O/YO$_2$ mole ratio of the synthesis mixture is at least about 2.

6. The process of claim 1, wherein the crystallization conditions include a temperature from about 100° C. to about 150° C.

7. The process of claim 1, wherein the crystalline material recovered in (iii) has a total surface area (as determined by the t-plot method for nitrogen physisorption) of at least about 750 m$^2$/g and/or an external surface area (as determined by the t-plot method for nitrogen physisorption) of at least about 350 m$^2$/g.

8. A process for producing a crystalline material having the MFI and/or MEL framework-type, the process comprising:
    (i) preparing a synthesis mixture capable of forming said crystalline material, said mixture comprising a source of an oxide of a tetravalent element Y, optionally a source of a trivalent element X, optionally a source of an alkali or alkaline earth metal (M), water, and a directing agent (Q$_2$) comprising 1,5-bis(N-tributylammonium)pentane dications, and/or 1,6-bis(N-tributylammonium)hexane dications;
    (ii) heating the mixture under crystallization conditions including a temperature from 80° C. to 220° C. and a time from about 4 hours to about 28 days until crystals of the crystalline material are formed; and
    (iii) recovering the crystalline material from step (ii).

9. The process of claim 8, wherein the synthesis mixture has a composition, in terms of mole ratios, within the following ranges:

| | |
|---|---|
| $YO_2/X_2O_3$ | at least about 20; |
| $H_2O/YO_2$ | about 2 to about 60; |
| $OH^-/YO_2$ | about 0.1 to about 0.8; |
| $M/YO_2$ | 0 to about 0.4; and |
| $Q_2/YO_2$ | about 0.05 to about 0.4. |

10. The process of claim 9, wherein the $H_2O/YO_2$ mole ratio of the synthesis mixture is about 10 or less.

11. The process of claim 9, wherein $M/YO_2$ mole ratio of the synthesis mixture is about 0.02 or less.

12. The process of claim 8, wherein the crystallization conditions include a temperature from about 100° C. to about 150° C.

\* \* \* \* \*